United States Patent
Gupta

(10) Patent No.: US 7,320,797 B2
(45) Date of Patent: Jan. 22, 2008

(54) ANTIAGING COSMETIC DELIVERY SYSTEMS

(75) Inventor: Shyam K Gupta, Scottsdale, AZ (US)

(73) Assignee: Bioderm Research, Scottsdale, AZ (US)

( * ) Notice: Subject to any disclaimer, the term of this patent is extended or adjusted under 35 U.S.C. 154(b) by 700 days.

(21) Appl. No.: 10/604,999

(22) Filed: Aug. 29, 2003

(65) Prior Publication Data

US 2005/0048008 A1  Mar. 3, 2005

(51) Int. Cl.
*A61K 8/02* (2006.01)
*A61K 8/04* (2006.01)
*A61K 8/06* (2006.01)

(52) U.S. Cl. ................... 424/401; 424/400
(58) Field of Classification Search .......... 424/400, 424/401

See application file for complete search history.

(56) References Cited

U.S. PATENT DOCUMENTS

| 6,436,416 | B2 * | 8/2002 | Granger et al. | 424/401 |
| 6,514,507 | B2 * | 2/2003 | Maignan et al. | 424/401 |
| 6,569,683 | B1 * | 5/2003 | Ochi et al. | 436/63 |

* cited by examiner

*Primary Examiner*—Shelley A. Dodson

(57) ABSTRACT

The present invention provides a comprehensive solution to the problems associated with natural topical aging via the incorporation of: (i) An Extra-cellular antioxidant or Free-radical neutralizing composition, and (ii) An Intra-cellular antioxidant or Free-radical neutralizing composition, and (iii) An Anti-inflammatory composition, and (iv) A collagen or fibrin boosting composition. It is preferred to also have the above incorporated in a suitable carrier base or topical delivery system for skin, nail, and hair beneficial applications.

8 Claims, No Drawings

ANTIAGING COSMETIC DELIVERY SYSTEMS

CROSS REFERENCE TO RELATED APPLICATIONS

Certain ion-pair compositions have been disclosed in unrelated prior applications by this inventor; U.S. patent application Ser. No. 10/249,701 (filed May 1, 2003), Ser. No. 10/439,349 (filed May 15, 2003), and Ser. No. 10/250,045 (filed May 30, 2003).

BACKGROUND OF INVENTION

The enhancement of physical appearance occupies greater focus in human life than nearly all other daily life-related concerns combined. There are far more consumer products available for the beautification of human body than for the treatment of human ailments. The improvement of skin tone and appearance is a growing, multibillion-dollar industry encompassing cosmetic, nutraceutical, pharmaceutical, and physical therapy disciplines. The consumer attention is focused on newest miracle ingredient in age-defying, anti-wrinkle, skin smoothing, skin brightening, and other similar antiaging compositions, such as those most recently disclosed in U.S. Patent Application 20030091665 (Lu et al.), 20030083380 (Yu et al.), 20020048798 (Avery et al.), 20020034527 (Streicher et al.), 20030091666 (Murad), 20030157138 (Eini et al.), U.S. Pat. No. 6,514,507 (Maignan et al.), U.S. Pat. No. 6,284,233 (Simon et al.), U.S. Pat. No. 6,436,416 (Grainger et al.), U.S. Pat. No. 6,224,850 (Breton et al.), U.S. Pat. No. 6,569,683(Ochi), and U.S. Pat. No. 5,885,596(Parab). All of these disclosures are based on single components or ingredients and do not provide a comprehensive scientific solution to the problems associated with the biology of natural aging of skin.

Based on the science of skin biology, the following four aspects are incorporated in the present invention to provide a comprehensive solution to the problems associated with natural skin aging, (i) An Extra-cellular antioxidant or Free-radical neutralizing composition, and (ii) An Intra-cellular antioxidant or Free-radical neutralizing composition, and (iii) An Anti-inflammatory composition, and (iv) A collagen or fibrin boosting composition.

It is preferred to also have the above incorporated in a suitable carrier base or topical delivery system.

The role of antioxidants and free radical neutralizing compositions in reducing skin aging process and skin wrinkle reduction is well known in the prior art. However, most of the antioxidants and free radical neutralizers that have been used in cosmetic compositions are absorbed quickly into skin. Although this does provide antioxidant or free radical neutralizing benefit to the intra-cellular structure of skin, this does reduce their efficacy in protecting upper surface of skin for any extended periods of time. It would thus be beneficial if antioxidants or free radical neutralizers can be temporarily bound to skin surface to retard their penetration into deeper layers of skin and provide extra-cellular antioxidant or free-radical neutralizing benefits.

The direct chemical bonding of beneficial ingredients to skin to provide extended term benefits (since such chemically bonded ingredients are not removed by washing or rubbing actions, and they generally will last until the skin is shed) has been disclosed in the prior art, for example U.S. Patent Applications 20030003119 (2003) and 20020172698 (Bekele). In order to achieve such chemical bonding, chemically reactive forms of bonding components, such as alkylating agents, diazonium salts, anhydrides, and acylating agents are used, the safety and toxicology of such chemically reactive agents themselves (several alkylating agents, diazonium compounds, and acylating agents are known to have carcinogenic, mutagenic, skin sensitizing, and allergenic properties) poses problems in their practical applications in the development of antiaging compositions. The temporary binding of beneficial compositions to skin, hair, and nail to extend the extra-cellular benefits of such compositions disclosed in the present invention thus offers a more convenient and safer methodology than permanent binding of compositions to skin.

The antioxidants and free radical neutralizers are also required for the protection of skin at the deeper skin renewal layers where fresh skin cells are generated. For this reason, an intra-cellular antioxidant or free radical neutralizer is also beneficial.

Anti-inflammatory compositions are required in the present invention to reduce the skin irritation caused by environmental, personal hygiene, body beautification, and dietary/personal habits situations. Skin irritation is known to cause the degradation of collagen, which results in skin wrinkles. The examples of environmental conditions that can cause skin irritation include dry air, UV, sunlight, free radicals, air pollutants, and such. The examples of personal hygiene conditions that can cause skin irritation include use of soap and cleansers, shaving and hair removal compositions, and such. The examples of body beautification that can cause skin irritation include fragrances, cosmetics, and other body decorative compositions. The examples of dietary/personal habits conditions that can cause skin irritation include the use of foods rich in fats that can enhance prostaglandin synthesis in the body, excessive use of tobacco, and alcohol, all of which are known to cause skin irritation.

Most anti-inflammatory agents function by decreasing prostaglandin production through their inhibition of cyclooxygenase-1 (COX-1), cyclooxygenase-2 (COX-2), and lipoxygenase-5 (LOX-5) enzymes. The uses of massage or vasodilatory ingredients for the removal of lactic acid from areas of inflammation are well known therapies. The initiation of inflammation by reactive oxygen species (such as superoxide anions) has been recognized. Recently, the role of Substance P in neurotransmission of pain from inflammatory response has been recognized. The inhibition of inflammatory cytokines in the development of new anti-inflammatory therapies is actively being studied. In addition, excessive nitric oxide (NO) production by activated macrophages has recently been implicated in several inflammatory diseases including arthritis. These aspects have been described in further detail in U.S. Pat. No. 5,494,668 (Patwardhan), U.S. Pat. No. 5,888,514 (Weisman), U.S. Pat. No. 5,854,291 (Laughlin), U.S. Pat. No. 5,916,565(Rose), and others.

Collagen and fibrin boosting compositions are also required in the present invention. It is well known that with natural aging process the production of collagen and fibrin slows down. This causes skin thinning, loss of skin elasticity, and formation of wrinkles. The inclusion of collagen or fibrin boosting compositions in any comprehensive antiaging treatment is thus of biological importance for skin regeneration.

It is well recognized in the scientific community that delivery systems are highly useful in cosmetics and pharmaceutical disciplines. In a recent article written by the present inventor (Cosmetic Delivery Systems, Household & Personal Products Industry, commonly known as HAPPI magazine, January 2003 issue, page 79) the definition and benefits of a number of prior art delivery systems have been discussed. A delivery system is thus a combination of both art and science that can improve the performance and consumer appeal of a consumer product or composition.

The present invention discloses a scientific combination of the above mentioned four principles required for healthy skin biology further incorporated in high-performance delivery systems to provide a comprehensive solution to the problems associated with natural skin aging such as wrinkles, loss of elasticity, discoloration, age spots, and such.

SUMMARY OF INVENTION

The present invention provides a comprehensive solution to the problems associated with natural topical aging via the incorporation of: (i) An Extra-cellular antioxidant or Free-radical neutralizing composition, and (ii) An Intra-cellular antioxidant or Free-radical neutralizing composition, and (iii) An Anti-inflammatory composition, and (iv) A collagen or fibrin boosting composition. It is preferred to also have the above incorporated in a suitable carrier base or topical delivery system for skin, nail, and hair beneficial applications.

DETAILED DESCRIPTION

The present invention provides a comprehensive solution to the problems associated with natural skin aging via the incorporation of: (i) An Extra-cellular antioxidant or Free-radical neutralizing composition, and (ii) An Intra-cellular antioxidant or Free-radical neutralizing composition, and (iii) An Anti-inflammatory composition, and (iv) A collagen or fibrin boosting composition. It is preferred to also have the above incorporated in a suitable carrier base or topical delivery system.

It is well known that most of the antioxidants and free radical neutralizers that have been used in cosmetic compositions for antiaging benefits are absorbed quickly into deeper layers of skin, and then transported away by bloodstream. Although this does provide antioxidant or free radical neutralizing benefit to the intra-cellular structures of skin, this does reduce their efficacy in protecting upper surface of skin for any extended periods of time. It would thus be beneficial if antioxidants or free radical neutralizers can be temporarily bound to skin surface to retard their penetration into deeper layers of skin and provide extra-cellular antioxidant or free-radical neutralizing benefits. Surprisingly, I have now found that the combination of one skin care composition with another skin care composition by an ion-pair mechanism, as shown in Equation 1, provides a solution to this problem. The ion-pair combinations thus formed are more bioavailable, have selective but synergistic benefits, and are economical to produce from commonly available ingredients.

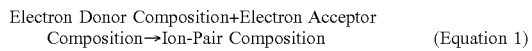
(Equation 1)

For example, quaternary ammonium compounds are commonly used in modern skin care compositions for various benefits that include conditioning, shine, skin smoothing, and such. These ammonium compounds, which are cationic in nature, also contain an anionic counter-ion as an ion-pair. For example, Crodasorb UV-HPP (Polyquaternium-59) is a polymeric quaternary ammonium composition in which chloride and methosulfate are attached as anionic counter-ions. It is well appreciated by those who are versed in this art that only the cationic part of such quaternary ammonium compositions provides skin care benefits such as preventing damage by UV, and protection of tensile strength, hydrophobicity, and protection of skin's natural color. In another example, Incroquat UV-283 (Cinnamidopropyltrimonium chloride), a UV-absorbing quaternary ammonium compound, provides protection from damage by UV and free radicals. In this example, the cationic Cinnamidopropyltrimonium moiety of this composition provides such benefits, and the anionic (chloride) part does not provide any skin beneficial effects. In these examples, if the anionic portions of these compositions were replaced by another anionic composition that has skin beneficial properties, then such compositions could be more beneficial to skin.

Sulfur amino acids, and compositions that contain a sulfhydryl (—SH) group, such as glutathione, are very important for human skin. The deposition of cysteine or glutathione on skin can provide benefits such as antioxidant and free radical protection. The deposition of such water-soluble compositions on skin or hair in any significant amount from a rinse-off consumer product, such as liquid soap or body wash, has been difficult in the prior art. The combination of a cationic quaternary ammonium composition, for example, Cinnamidopropyltrimonium chloride (which is disclosed in U.S. Pat. Nos. 5,633,403 and 5,601, 811) with an anionic cysteine derivative (Equation 2), surprisingly, solves this problem.

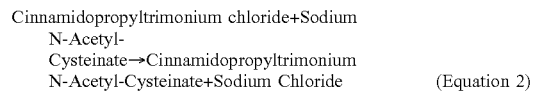
(Equation 2)

To illustrate this point further, glutathione, a sulfur peptide known to be skin beneficial antioxidant, can be combined in an ion-pair mode with a polymeric quaternary ammonium composition, such as Polyquaternium-59, to produce Polyquaternium-59 glutathionate (as shown in Equation 3), a new ion-pair ingredient that has antioxidant and skin smoothing properties with better deposition on skin due to the interaction of its cationic charge with the anionic charge of human skin.

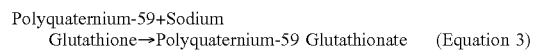
(Equation 3)

Similarly, certain vitamins, such as vitamin C (ascorbic acid) are well known for their antioxidant protection, collagen boosting, and free radical neutralizing functions. Vitamin C has been used extensively in antiaging compositions, such as those disclosed by the present inventor in U.S. patent application Ser. No. 10/223,671 (filed August 16, 2002) and Ser. No. 10/265,000 (filed Oct. 4, 2002). However, vitamin C generally absorbes into the deeper layers of skin in all prior art compositions for antiaging benefits. The present invention provides a new methodology whereby vitamin C can be deposited and be retained on the surface layers of skin for its extended benefits in providing extra-cellular antioxidant or free-radical neutralizing functions for antiaging benefits. This is exemplified by the preparation of Polyqyaternium-59 Ascorbate, from Polyquaternium-59 and sodium ascorbate, according to Equation 4. Polyquaternium-59 ascorbate thus provides extra-cellular antioxidant, free radical neutralizing, and skin smoothing benefits, all by one single composition.

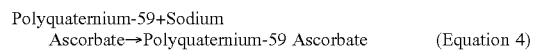
(Equation 4)

The ion-pair compositions made from quaternary ammonium compounds and certain antioxidant and free radical neutralizing components, as exemplified above, bind preferentially with the outer layers of skin. Their absorption into the deeper layers of skin is thus greatly retarded, hence they provide extra-cellular antioxidant or free-radical neutralizing functions for antiaging benefits.

Lipoic acid is well known for its antiaging benefits, for example as disclosed in U.S. Pat. No. 5,709,868(Perricone). It is also rapidly absorbed into deeper layers of skin by prior art antiaging disclosures. The methodology of the present invention provides a solution to this problem by converting lipoic acid into an ion-pair cationic-bound derivative, as per Equation 5. Stearalkonium lipoate is retained preferentially on the extra-cellular surfaces of skin due to the binding of its cationic form with anionically charged skin surface.

Stearalkonium chloride+Sodium
Lipoate→Stearalkonium lipoate (Equation 5)

Carnosine is another well known intra-cellular antioxidant, which can be converted into an extra-cellular antioxidant by the present invention, as shown in Equation 6.

Polyquaternium-10+Sodium
Carnosinate→Polyquaternnium-10 Carnosinate (Equation 6)

In the above example, the preparation of Sodium derivatives of antioxidant or free-radical neutralizing compositions is very simple from commonly available ingredients, for example the preparation of Sodium N-Acetyl-Cysteinate, as illustrated in Equation 7.

N-Acetyl-Cysteine+Sodium Hydroxide→Sodium
N-Acetyl-Cysteinate+Water (Equation 7)

The mixtures of several extra-cellular antioxidant compositions can be prepared in-situ from commonly available ingredients, as shown in Equation 8.

Polyquaternium-59+Sodium Ascorbate+Sodium
Acetyl Cysteinate+Sodium
Lipoate→Polyquaternium-59 Ascorbate+
Polyquaternium-59 Acetyl Cysteinate+
Polyquaternium-59 Lipoate (Equation 8)

It should be evident that previously unknown skin, nail, and hair beneficial ion-pair compositions in a nearly unlimited number of combinations can be prepared according to the teachings of the present invention, as illustrated in Equations 1 to 8. The examples include, but not limited to Cinnamidopropyltrimonium N-Acetyl-Cysteinate, Cinnamido-propyltrimonium ascorbate, Cinnamidopropyltrimonium glutathionate, Cinnamidopropyltrimonium carnosinate, Cinnamidopropyltrimonium lipoate, Cinnamidopropyltrimonium niacinate, Cinnamidopropyltrimonium biotinate, Cinnamidopropyltrimonium pantothenate, Polyquaternium-59 Glutathionate, Polyquaternium-59 ascorbate, Polyquaternium-59 carnosinate, Polyquaternium-59 lipoate, Polyquaternium-59 niacinate, Polyquaternium-59 pantothenate, Polyquaternium-59 N-acetyl-cysteinate, Polyquaternium-59 biotinate, Stearalkonium ascorbate, Stearalkonium biotinate, Stearalkonium N-acetyl-cysteinate, Stearalkonium lipoate, Stearalkonium niacinate, Stearalkonium carnosinate, Stearalkonium glutathionate, and Stearalkonium pantothenate.

The importance of intra-cellular antioxidants in antiaging compositions has received spotlight in recent years. The incorporation of botanical antioxidants in cosmetic products is gaining popularity due to anti aging and other skin tone enhancement benefits, concordant to their use as nutritional supplements. Cosmetic products formulated with familiar antioxidants (vitamin E, Coenzyme Q10, ascorbic acid, lipoic acid, and soy isoflavones, etc.) have appeared in the marketplace with promissory claims. The design of a topical antioxidant product offers challenges: A wide spectrum antioxidant product should control intra-cellular oxidation resulting from biochemical mechanisms including oxygen, free radicals, UV, atmospheric pollutants, oxidative enzymes, catabolic oxidation, and chemical oxidation. The selection of functional intra-cellular antioxidants and free radical neutralizers to control complex, frequently inter-related biochemical oxidation mechanisms, and design of topical delivery systems to assure bioavailability via absorption through skin are of paramount importance.

A combination of antioxidants is more effective than a single antioxidant on an equal weight basis due to antioxidant cascade mechanism. It is well known that antioxidants belong to various chemical classes, such as polyphenols, carotenoids, flavonoids, and such. Some examples follow. (Chemical class is indicated in parentheses.) Rutin (flavone), Quercetin (flavone), Hesperidin (flavone), Diosmin (flavone), Mangiferin (xanthone), Mangostin (xanthone), Cyanidin (carotenoid), Astaxanthin (carotenoid), Xanthophyll (carotenoid), Lycopene (carotenoid), carotene (carotenoid), resveratrol, (polyphenol), tetrahydrocurcumin (polyphenol), rosmarinic acid (polyphenol), ellagic acid (polyphenol), hypericin (polyphenol), chlorogenic acid (polyphenol), oleuropein (polyphenol), lipoic acid (disulfide), glutathione-oxidized (disulfide), cystine (disulfide), N-acetyl-cystine (disulfide), glutathione-reduced (sulfhydryl), cystein (sulfhydryl), and N-acetyl-cysteine (sulfhydryl).

The present invention proposes that a combination of antioxidant ingredients should be included from different chemical classes to control intra-cellular oxidation resulting from various biochemical mechanisms. Most of these antioxidants also possess anti-inflammatory and antimicrobial properties. The total quantity of antioxidants should be balanced carefully, as an excessive amount of antioxidants may have an opposite, prooxidant effect resulting in poor stability and performance of the product. The use of antioxidant synergists offers additional advantages. The key function of such synergist is to reconvert the antioxidant free radical into its original non-radical state followed by its self-destruction into neutral, harmless molecules. Hydroxy acids (citric, ascorbic, tartaric, etc.), frequently used for this purpose. Coenzyme Q10, vitamin C, and quercetin have also been reported as synergists.

Anti-inflammatory compositions are required in the present invention to reduce the skin irritation caused by environmental, personal hygiene, body beautification, and dietary/personal habits situations. It is to be noted that a mixture of two or more anti-inflammatory compositions, especially those that belong to different biochemical mechanism classes, is more beneficial than corresponding equal weight amounts of a single ingredient. This is due to various different biochemical mechanisms by which such anti-inflammatory compositions provide their beneficial effect. A number of both synthetic and natural compositions have thus become available; some of such examples follow (the biochemical mechanisms of their action are indicated in the parentheses). Ginger Root, or *Zingiber Officinale* Root Extract (COX-2 inhibitor), Galanga, or *Alpinia Officinarum* Extract (LOX-5 inhibitor), Turmeric, or *Curcuma Longa* Root Extract (Superoxide inhibitor), Mango Ginger, or *Curcuma amada* (Unknown mechanism), *Capsicum*, or *Capsicum Annuum* Extract (Substance P inhibitor, Vasodilation, Superoxide inhibitor), Clove Family, or *Syzygium Aromaticum* Extract (COX-1, COX-2 inhibitor), *Evodia*, or *Evodia Rutaecarpa* Fruit Extract, (COX-2 inhibitor), *Boswellia*, or *Boswellia Serrata* Extract (LOX-5 inhibitor), SAMe, or S-Adenosylmethionine (Catecholamine metabolism), *Euco-*

*mis*, or *Eucomis L"Herit* (COX-1 inhibitor), *Celastrus*, or *Celastrus orbiculatus* (COX-1 inhibitor), *Tithonia*, or *Tithonia diversifolia* (Cytokine inhibitor), *Kochia*, or *Kochia Scoparia* Extract (COX-2 inhibitor), *Scoparia*, or *Scoparia dulcis* Extract (Analgesic), *Qiang Huo*, or *Notopterygium incisum* (COX-1, LOX-5 inhibitor), Cinnamon, or *Cinnamonum cassia* (Nitric oxide scavenger), Mexican Bamboo, or *Polygonum cuspidatum* (Nitric Oxide scavenger), Ogon, Baikal Scullcap, or *Scutellaria baicalensis* (COX-2 inhibitor), *Coptis, Xianglian,* or *Coptis chinenesis* (Nitric oxide inhibitor), *Psoralea, Rumex, Baccharis, Feverfew, Vitis, Stephania* (unknown mechanisms), and *Corydalis*, or *Corydalis Turtschaninovii* Root Extract (Analgesic).

Ginger has been in use in Ayurvedic and Tibetan medicine for centuries. Ginger extracts are known to increase peripheral blood flow with a feeling of warming and tingling sensation. Ginger contains essential oils and spicy substances such as gingerol, shogaol, zingerone, and capsaicin; those spicy substances are principally responsible for its pain relieving properties. Recent scientific studies suggest that inhibiting the COX-2 enzyme may be an effective way to reduce inflammation without the side effects associated with irreversible COX-1 inhibition. Ginger inhibits COX-2, and also 5-lipoxygenase (LOX-5) enzyme.

Turmeric (*Curcuma longa*) rhizomes contain curcumin and its derivatives (curcuminoids) that are bright yellow in color. Their hydrogenated derivatives, tetrahydrocurcuminoids, are nearly colorless materials. All of these ingredients possess excellent anti-inflammatory activity. Tetrahydrocurcuminoids offer advantages in topical cosmetic applications due to their lack of color. The steam distillation of turmeric rhizomes provides turmeric oil, reported to possess excellent anti-inflammatory activity.

Galanga (*Alpinia officinarum*), also known as Galangal or Chinese Ginger, is native to China, Thailand, and India. It contains essential oils, gingerols, and a group of pungent substances, diarylheptanoids. The studies have shown diarylheptanoids (and analogous phenyl alkyl ketones) to possess excellent anti-arthritic properties due to their arrest of prostaglandin biosynthesis via inhibition of 5-lipoxygenase. *Capsicum*, Capsaicin: The ancient Maya folk-healers used cayenne pepper (*Capsicum frutescence*) for the treatment of toothache and general body pain. In modern Western medicine, *capsaicin* has been used to treat pain associated with neuralgia, neuropathy, osteoarthritis, rheumatoid arthritis, bladder pain, and stomach pain. *Capsaicin* is the active analgesic ingredient present in *capsicum* preparations. It is a topical analgesic that may inhibit the synthesis, transport, and release of substance P, a neurotransmitter of pain. *Capsaicin* is also a vasodilator.

Clove Family. Clove oil and clove buds have been in use for the treatment of toothache and muscular pains since ancient times. A number of plants in this family, notably *Syzygium aromaticum, Syzygium corynocarpum,* and *Syzygium mallacense*, are known to contain pain-relieving constituents. Eugenol, a vasorelaxant and analgesic constituent of *Syzygium aromaticum*, also possesses strong anti-inflammatory activity. The extracts of *Syzygium corynocarpum* and *Syzygium malaccense* inhibit prostaglandin biosynthesis via blocking of COX-1 and COX-2 enzymes. The extract from the bark of *Syzygium cumini* has been shown to possess excellent antiinflammatory activity without any gastric side effects. Acetyl eugenol, a component of clove oil, has recently been shown to alter arachidonic acid metabolism, resulting in reduced formation of thromboxane.

Evodia: This herb has been used for dysentery in Chinese medicine (Wu Zhu Yu) since ancient times. Rutaecarpine, obtained from *Evodia rutaecarpa*, is a new class of recently introduced anti-inflammatory ingredients that directly inhibits COX-2 enzyme. Antinociceptive and antiinflammatory activities of the extracts of this plant have recently been reported. Evodiamine, and its analogs present in *Evodia rutaecarpa* also possess vasodilatory and analgesic activity.

Frankincense, *Boswellia*: Guggal (*Boswellia serrata*) has been used for the treatment of arthritis in Ayurvedic medicine for centuries. Frankincense, myrrh, and gold were among three presents brought by the Wise Men to the infant Christ. It is interesting that all three of these have been used in the treatment of gout and arthritis in ancient history of medicine. *Boswellia* is currently one of the most popular alternative medicines for inflammation. Recent research has identified four key ingredients (grouped as boswellic acids) that are responsible for the anti-inflammatory action of *Boswellia serrata* extracts. Recent research has firmly established that Boswellic acids and their derivatives are specific inhibitors of leukotriene synthesis by their direct interaction with 5-lipoxygenase.

SAMe (S-Adenosylmethionine): It has received wide interest for the treatment of osteoarthritis since its discovery in 1952. This substance, present in all living organisms, is required for over 40 biochemical functions in human body. It has been proven to enhance the formation of cartilage, and provide pain relieving anti-inflammatory action.

Eucomis: South African traditional medicine has extensively utilized the extracts of bulb, leaves, and root of this plant for pain, inflammation, and fever. Recent work has shown that the extracts from bulb have the highest level of COX-1 inhibitory activity.

Celastrus: This oriental folk medicine has been used for rheumatoid arthritis. Recent work has identified strong COX-1 activity ascribed to epiafzelechin, a member of flavan-3-ols, present in this herb. *Tithonia*: The extracts of *Tithonia* are used in Central America for the treatment of haematomas. Recent work has shown the constituents of this extract, diversifolin and tirotundin, to possess anti-inflammatory activity. Interestingly, the anti-inflammatory activity was from the inhibition of the synthesis of inflammatory mediators such as cytokines and chemokines.

*Scoparia*: The herb *Scoparia dulcis* is used in Brazilian folk medicine to treat bronchitis, gastric disorders, hemorrhoids, insect bites and skin wounds, and in oriental medicine to treat hypertension. Recent studies have shown that extracts of *Scoparia dulcis* have analgesic, anti-inflammatory, and sympathomimetic activity.

*Qiang Huo*: The root extracts of this Chinese medicinal herb traditionally used for arthritis and joint pain have recently been shown to possess COX-1 and LOX-5 inhibitory activity.

Cinnamon: The traditional use of cinnamon as a vasodilator for pain and inflammation in the Middle Eastern and other countries has long been practiced. Recent disclosures have confirmed the anti-nociceptive and anti-inflammatory activity of cinnamon extract via its direct scavenging of nitric oxide and peroxynitrite.

*Polygonum*: This herb is more commonly known as Mexican Bamboo (Mexico) and Hu Zhang (China). Various species of *Polygonum* have recently been identified to contain anti-inflammatory constituents that modulate the production of NO by activated macrophages. Recent results suggest that *Polygonum tinctorium* extract may be a potential therapeutic modulator of NO synthesis in various pathological conditions.

*Ogon* (Ougon): *Scutellaria*, used in Japanese Kampo herbal medicine (*Ogon*), China, (Sanhuang), and in Baikal region of Russia, has shown anti-inflammatory, antihepatitis, antibacterial, antiviral, anti-tumor, and anti-oxidant activity. The anti-inflammatory activity is ascribed to its active components, baicalin, baicalein and wogonin. In a recent study, wogonin tested as a direct inhibitor of COX-2, NO-production, and prostaglandin production, indicating its potential use in the treatment of topical inflammatory diseases. Baicalin, in another study, showed chemokine inhibiting activity. Baikalein has shown LOX-5 inhibiting activity.

Coptis: Coptis, a Chinese herbal medicine (Xianglian) also used in Japan, is well known for its antibacterial properties due to its high berberine content. It also contains several lignans (isolariciresinol, lariciresinol glycoside, pinoresinol, pinoresinol glycoside, and syringaresinol glycoside) with anti-inflammatory properties. Woorenosides, isolated from *Coptis japonica*, have shown anti-inflammatory activity via their inhibition of NO production.

*Psoralea glandulosa*: An ancient Persian medicine, *Psoralea glandulosa* contains bakuchiol, cyclobakuchiols, and angelicin that possess anti-pyretic and antiinflammatory activity. *Psoralea corylifolia*, an Ayurvedic medicine in India (Babchi) and BuGuZhi in China, possesses anti-inflammatory, anti-pyretic, and analgesic activity due to its bavachinin content. Bakuchiol, recently isolated from the same plant, inhibits NO synthase gene, with implications for its anti-inflammatory activity.

*Rumex patientia* (Dock) has shown antiinflammatory activity.

*Baccharis*: Several species of *Baccharis* have shown analgesic and anti-inflammatory activity, principally due their inhibition of prostaglandin biosynthesis.

Feverfew: This phytopharmaceutical (*Tanacetum parthenium*) is well known for its fever and migraine alleviation benefits. Recently, its anti-nociceptive and anti-inflammatory activities, due to its LOX-5 and COX inhibition, have been reported Vitis: The grape family is well known for its potent antioxidant constituents, especially procyanidins and resveratrol. Recently, tetramers of resveratrol found in Vitis amurensis, have been found to possess strong anti-inflammatory activity via their inhibition of leukotriene biosynthesis. This is not surprising, as several antioxidants are also known to possess anti-inflammatory activity: This property may be due to their inhibitory effect on LOX and COX enzymes.

Stephania: Stephania has long been used in Korea as an analgesic and anti-inflammatory agent for joint swelling. Tetrandrine, an alkaloid found in *Stephania japonica* is well known for its anti-inflammatory activity. Cepharanthine, an alkaloid found in *Stephania cepharantha*, has revealed vasodilatory effects with enhanced microcirculation.

*Tinospora*: Ayurvedic and Islamic practitioners in India have used *Tinospora cardifolia* for liver jaundice, various skin diseases, rheumatism, fever, and syphilis. Clinical studies conducted with human arthritis have demonstrated its anti-inflammatory properties. The inhibition of nitric oxide synthesis appears to be a factor for this activity.

Additional examples of anti-inflammatory compositions include Horse Chestnut Extract (*Aesculus hippocastanum* extract)), *Esculin, Escin, Yohimbine, Capsicum Oleoresin, Capsaicin*, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum, Fenugreek*), *Emblica* extract (*Phyllanthus emblica* extract), Asiaticoside (*Centella asiatica* extract), *Boswellia* Extract (*Boswellia serrata*), Ginger Root Extract (*Zingiber Officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), *Amni visnaga* extract, extract of Red Vine (Vitis-Vinifera) leaves, apigenin, phytosan, and luteolin.

Collagen and fibrin boosting compositions are also required in the present invention. It is well known that with natural aging process the production of collagen and fibrin slows down. This causes skin thinning, loss of skin elasticity, and formation of wrinkles. The inclusion of collagen or fibrin boosting compositions is thus of biological importance for skin regeneration. The collagen or fibrin boosting composition can be selected from, but not limited to, glucosamine, N-acetyl-glucosamine, chondroitin, algae extracts, chitosan, niacinamide, niacinamide derivatives, copper nucleotides, zinc nucleotides, manganese nucleotides, glutathione, carnosine, vitamin C, vitamin E, vitamin A, Coenzyme Q10, lipoic acid, dimethylamino ethanol, Ascorbic acid, Ascorbic acid derivatives, Glucosamine ascorbate, Arginine ascorbate, Lysine ascorbate, Glutathione ascorbate, Nicotinamide ascorbate, Niacin ascorbate, Allantoin ascorbate, Creatine ascorbate, Creatinine ascorbate, Chondroitin ascorbate, Chitosan ascorbate, DNA Ascorbate, Carnosine ascorbate, Vitamin E, various Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), Lipoic acid, Niacinamide lipoate, Glutathione, Andrographolide (*Andrographis paniculata*), Carnosine, Niacinamide, Potentilla erecta extract, Polyphenols, Grapeseed extract, Pycnogenol (Pine Bark extract), copper nucleotide, zinc nucleotide, manganese nucleotide, copper glucoside, zinc glucoside, manganese glucoside, and combinations thereof.

Since living parts of hair and nail are also very similar to skin in aging process, the compositions of the present invention are also useful for hair and nail antiaging compositions.

EXAMPLES

The following examples are presented to illustrate presently preferred practice thereof. As illustrations they are not intended to limit the scope of the invention. All quantities are in weight %.

Example 1

Preparation of Sodium N-Acetyl-Cysteinate, as per Equation 7 (1) N-Acetyl-Cysteine 15.1 (2) Deionized Water 76.9 (3) Sodium Hydroxide (50% solution) 8.0 Procedure. Mix (1) and (2) to a clear solution. Add (3) and mix. A clear, 17.3% solution of Sodium N-Acetyl-Cysteinate is obtained. On evaporation of water under vacuum, a white solid crystalline composition of Sodium N-Acetyl-Cysteinate (100% molecular activity level) is obtained.

Example 2

Preparation of Cinnamidopropyltrimonium N-Acetyl-Cysteinate, as per Equation 2 (1) Sodium N-Acetyl-Cysteinate 17.3 (100% molecular activity level) (2) Cinnamidopropyltrimonium chloride (Molecular Weight 283, molecular activity level 70%) 40.4 (3) Deionized water 42.3 Procedure. Mix (1) and (2) to a clear solution. Add (3) and mix. A light amber solution is obtained, which contains 39.7% of Cinnamidopropyltrimonium N-Acetyl-Cysteinate.

Example 3

Preparation of Polyquaternium-59 Glutathionate, as per Equation 3 (1) Polyquaternium-59 10.0 (65% active level commercial solution) (2) Deionized water 85.4 (3) Glutathione 3.0 (4) Sodium Hydroxide (50%) 1.6. Procedure. Mix (2) and (3) to a clear solution. Add (4) and mix. Add (1) and mix. A light brown solution of Polyquaternium-59 Glutathionate (about 8.0% "active" in water) is obtained.

Example 4

A high potency antiaging serum composition. (1) Escin 2.5 (2) Esculin 2.5 (3) Ruscogenins 2.5 (4) *Boswellia serrata* extract 2.0 (5) Methylpropanediol 67.0 (6) Vitamin K 0.5 (7) Tetrahydrocurcumin 0.5 (8) *Coleus forskohlii* extract 10 (9) Water 10 (10) Phenoxyethanol 0.5 (11) Stearalkonium ascorbate 2.0. Procedure. All ingredients were mixed with heating at 50 to 60C. A serum product was obtained which was quick absorbing.

Example 5

An Anti-Aging Night Cream Composition (1) Water 81.15 (2) Carbomer 0.2 (3) GMS-SE 2.0 (4) Stearic Acid 3.0 (5) Cetyl Alcohol 1.5 (6) Glycerin 1.0 (7) Jojoba Oil 0.1 (8) Sweet Almond Oil 0.1 (9) Sesame Oil 0.2 10) Apricot Kernel Oil 0.2 (11) Panthenol 0.1 (12) Glydant Plus (Preservative) 0.2 (13) Dimethicone 2.0 (14) Vitamin E Acetate 0.1 (15) Vitamin A Palmitate 0.1 (16) Cinnamidopropyltrimonium ascorbate 5.0 (17) Niacinamide lipoate 2.0 (18) Darutoside 0.5 (19) Glutathione 0.05 (20) Fragrance 0.15 (21) Botanical Extract 0.25. Procedure. All ingredients, except fragrance and botanical extract, were mixed and heated at 70 to 80C, then cooled to room temperature. Fragrance, and botanical blends were all added to the main batch and the batch mixed. An off-white cream was obtained.

Example 6

Shampoo Composition (1) Sodium Lauryl Ether Sulfate 35.0 (2) Deionized Water 55.4 (3) Cinnamidopropyltrimonium N-Acetyl-Cysteinate 5.0 (4) Preservatives 0.5 (5) Laureth-3 2.5 (6) Rosmarinic acid 0.1 (7) Darutoside 1.0 (8) Niacinamide ascorbate 0.5. Procedure. Mix (1) to (8) to a clear solution. A shampoo composition is obtained.

Example 7

Antiaging Skin Cream Composition (1) Deionized water 80.25 (2) Cetearyl alcohol (and) Dicetyl phosphate (and) Ceteth-10 phosphate 5.0 (3) Cetyl alcohol 2.0 (4) Glyceryl stearate (and) PEG-100 stearate 4.0 (5) Caprylic/capric triglyceride 5.0 (6) Rosmarinic acid 0.1 (7) Tetrahydrodiferuloylmethane 0.1 (8) Glutathione 0.1 (9) Diosmin 0.05 (10) Resveratrol 0.05 (11) Andrographolide 0.05 (12) Hesperetin 0.05 (13) Mangiferin 0.05 (14) Fragrance 0.5 (15) Cetrimonium ascorbate 1.5 (16) Benzalkonium N-acetyl-cysteinate 0.5 (17) Phenoxyethanol 0.5 (18) Propyl paraben 0.2 (19) Sodium hydroxide qs. (for pH adjustment). Procedure. Mix 1 to 5 and heat to 75-80° C. Adjust pH to 4.0

4.5. Cool to 35-40° C. with mixing and homogenize. Add 6 to 18 with mixing. Adjust pH to 4.0-4.5, if necessary. White to off-white cream.

Example 8

Antiaging Nail Protectant Composition (1) Deionized water 30.5 (2) Denatured alcohol 60.00 (3) Shellac 5.0 (4) Bamboo Extract 1.0 (5) Niacinamide Ascorbate 1.0 (6) Cinnamidopropyltrimonium biotinate 0.5 (7) Cinnamidopropyltrimonium N-Acetyl-Cysteinate 1.0. (8) *Boswellia serrata* extract 0.5 (9) Vitamin K 0.1 (10) Tetrahydrocurcumin 0.4. Procedure. Mix (2), (3), (8), (9), and (10) to a clear solution. Mix (1), (5), (6), and (7) separately to a solution and add to main batch and mix. Add all other ingredients and mix. A light amber solution is obtained.

Example 9

Antiaging Hair Tonic Composition (1) Deionized water 66.1 (2) PEG-6 20.0 (3) Glycerin 2.0 (4) Preservative 0.5 (5) Polysorbate-20 4.0 (6) Fragrance 0.2 (7) Amodimethicone 2.0 (8) Cinnamidopropyltrimonium N-Acetyl-Cysteinate 2.0 (9) Yohimbine hydrochloride 0.5 (10) Mangiferin 0.1 (11) Rosmarinic acid 0.1 (12) N-Acetyl-glucosamine 1.0. Procedure. Mix all ingredients to a clear solution.

Example 10

Antiaging Eye Gel Composition (1) Deionized water 76.54 (2) Preservative 0.5 (3) Niacinamide Lactate 3.7 (4) Glutathione, reduced 0.01 (5) Arctostaphylos *Uva Ursi* Leaf Extract (and) *Mitracarpus Scaber* Extract 0.1 (6) Ammonium Acryloyldimethyltaurate/VP Copolymer 2.0 (7) Carnosine 15.0 (8) Cyclomethicone (and) Dimethicone Crosspolymer-3 2.0 (9) Polyquaternium-46 biotinate 0.1. Procedure. Mix all ingredients till a clear gel is formed.

Example 11

Antiaging Skin Cream Composition (1) Deionized water 76.8 (2) Acrylates/C10-30 Alkyl Acrylate Crosspolymer 0.2 (3) Carbomer 0.3 (4) Sodium hydroxide 0.1 (5) Sodium Stearyl Phthalamate 1.0 (6) EDTA 0.2 (7) Caprylic/Capric Triglyceride 5.0 (8) C12-15 Alkyl Benzoate 5.0 (9) GMS-SE 0.5 (10) Cetyl Alcohol 2.0 (11) Preservative 0.5 (12) Escin 0.1 (13) Esculin 0.1 (14) *Boswellia serrata* extract 0.1 (15) Vitamin K 0.1 (16) Horse Chestnut Extract 0.5 (17) Methylpropanediol 5.0 (18) Cinnamidopropyltrimonium ascorbate 2.5. Procedure. Mix (1) to (11) and heat at 70 to 80C. Cool main batch to 40 to 50C. Mix (12) to (17) separately and heat at 40 to 50C to a solution and add to main batch. Cool to room temperature, add (18), mix, and adjust pH to 6.5 to 7.0 with sodium hydroxide solution.

I claim:

1. A skin antiaging cosmetic delivery system for topical application comprised of; (i) A quaternary ammonium Extracellular antioxidant agent, and (ii) An Intracellular antioxidant agent, and (iii) An Antiinflammatory agent, and (iv) A collagen boosting agent, and (v) A carrier base.

2. A delivery system according to claim 1, wherein quaternary ammonium Extra-cellular antioxidant agent is Cinnamidopropyl Trimonium N-Acetyl-Cysteinate.

3. A delivery system according to claim 1, wherein intracellular antioxidant agent is copper nucleotide.

4. A delivery system according to claim 1, wherein anti-inflammatory agent is apigenin.

5. A delivery system according to claim 1, wherein collagen boosting agent is carnosine ascorbate.

6. A delivery system according to claim 1, wherein a carrier base is selected from traditional water and oil emulsions, suspensions, colloids, microemulsions, clear solutions, suspensions of nanoparticles, emulsions of nanoparticles, or anhydrous compositions.

7. A delivery system according to claim 1, wherein skin cleansers, surfactants, skin conditioning agents, hair conditioning agents, vitamins, hormones, minerals, plant extracts, anti-inflammatory agents, concentrates of plant extracts, emollients, moisturizers, skin protectants, humectants, silicones, skin soothing ingredients, analgesics, skin penetration enhancers, solubilizers, anesthetics, colorants, perfumes, preservatives, seeds, seed nut shells, silica, clays, beads, luffa particles, polyethylene balls, mica, pH adjusters, processing aids, fragrances, and their combinations, are included.

8. A carrier base according to claim 1, wherein carrier base is an anhydrous composition.

* * * * *